United States Patent [19]

Oeckl et al.

[11] 4,395,371
[45] Jul. 26, 1983

[54] PROCESS FOR THE PREPARATION OF 2-HALOGENO-3-SULPHONYL-ACRYLONITRILES

[75] Inventors: Siegfried Oeckl; Gero Zahl, both of Cologne; Walter Radt, Krefeld, all of Fed. Rep. of Germany

[73] Assignee: Bayer Aktiengesellschaft, Leverkusen, Fed. Rep. of Germany

[21] Appl. No.: 310,701

[22] Filed: Oct. 13, 1981

[30] Foreign Application Priority Data

Oct. 31, 1980 [DE] Fed. Rep. of Germany ....... 3041154

[51] Int. Cl.$^3$ ................. C07C 120/00; C07C 121/30; C07C 121/48; C07C 121/70
[52] U.S. Cl. ................................ 260/464; 260/465 F; 260/465 G; 260/465.6; 260/465.7; 424/304
[58] Field of Search ................. 260/465.7, 465 G, 464

[56] References Cited

U.S. PATENT DOCUMENTS 2,694,726 11/1954 Anspon ......................... 260/465.7 X
3,437,685 4/1969 Brust ................................... 560/150
4,079,148 3/1978 Oeckl et al. ................... 260/465.7 X
4,238,405 12/1980 Felix ..................................... 260/464

FOREIGN PATENT DOCUMENTS 2500265 7/1976 Fed. Rep. of Germany ... 260/465.7
2296623 1/1976 France .

OTHER PUBLICATIONS

"The Chemistry of Acrylonitrile", Cyanamid, 2nd ed., 1959, pp. 242-243.
Achmatowicz, et al.; Roczniki Chemii, 30, (1956), pp. 243-251.
Methoden der Organischen Chemie—(Houben-Weyl), Georg Thieme Verlag, Stuttgart, Band V/1b, 1972, pp. 168-172.

*Primary Examiner*—Joseph Paul Brust
*Attorney, Agent, or Firm*—Sprung, Horn, Kramer & Woods

[57] ABSTRACT

The preparation of a 2-halogeno-3-sulphonyl acrylonitrile from a 2,2-dihalogeno-3-sulphonyl propionitrile and water and the use of the product as a microbicidal agent are disclosed.

3 Claims, No Drawings

PROCESS FOR THE PREPARATION OF 2-HALOGENO-3-SULPHONYL-ACRYLONITRILES

The invention relates to a process for the preparation of 2-halogeno-3-sulphonyl-acrylonitriles.

It is known from German Offenlegungsschrift No. 2,500,265 that 2-halogeno-3-sulphonyl-acrylonitriles are obtained from 2,2-dihalogeno-3-sulphonyl-propionitriles by cleavage of hydrogen halide with base, such as triethylamine, alkali metal hydroxides, alkali metal alcoholates or alkali metal salts of carboxylic acids.

A process for the preparation of 2-halogeno-3-sulphonyl-acrylonitriles of the formula $$R^1-SO_2-CH=CX^1-CN \qquad (I)$$

wherein $R^1$ denotes optionally substituted aryl, aralkyl, alkyl or cycloalkyl and $X^1$ denotes halogen, has been found, which is characterised in that 2,2-dihalogeno-3-sulphonyl-propionitriles of the formula $$R^1-SO_2-CH_2-CX_2^1-CN \qquad (II)$$

wherein $R^1$ and $X^1$ have the meaning given above, are treated with water, if appropriate in the presence of an organic solvent and, if appropriate, at elevated temperature.

Aryl radicals which may be mentioned are aromatic radicals with 6 to 18 carbon atoms, which can be linearly linked with one another or condensed. Phenyl, biphenyl and naphthyl are mentioned as examples. Phenyl is preferably mentioned. Other aryl radicals, e.g. aralkyl, which may be mentioned are radicals with 7 to 14 carbon atoms, in which the aromatic part of the aralkyl can contain up to 10 carbon atoms and the aliphatic part up to 6 carbon atoms. Ethylphenyl, benzyl and naphthylmethyl are mentioned as examples. Benzyl is preferably mentioned.

Alkyl radicals which may be mentioned are straight-chain or branched hydrocarbon radicals with 1 to 12 carbon atoms, preferably lower alkyl radicals with 1 to 6 carbon atoms. Methyl, ethyl, propyl, isopropyl, butyl, isobutyl, pentyl, isopentyl, hexyl, isohexyl, octyl, isooctyl and undecyl may be mentioned as examples. Methyl and ethyl may be preferably mentioned.

Cycloalkyl radicals which may be mentioned are hydrocarbon radicals with 6 to 17 carbon atoms, for example cyclopentyl, cyclohexyl, and the decalin radical.

Fluorine, chlorine, bromine and iodine, preferably chlorine and bromine, particularly preferably chlorine, may be mentioned as halogen.

The radicals can be substituted by further radicals which do not change under the conditions according to the invention. Nitro groups, cyano groups, alkoxy groups with 1 to 4 carbon atoms, such as methoxy, ethoxy, propoxy, iso-propoxy, butoxy and iso-butoxy, and halogens, such as fluorine, chlorine, bromine and iodine may be mentioned as examples.

The 2,2-dihalogeno-3-sulphonyl-propionitriles employed in the process according to the invention are known from the U.S. Pat. No. 3,437,685 and German Offenlegungsschrift No. 2,500,265. Thus, for example, by reaction of 3-sulphonyl-propionitriles with chlorine or bromine, 2,2-dichloro- or 2,2-dibromo-3-sulphonyl-propionitriles can be prepared.

The 3-sulphonyl-propionitriles used in this reaction are known from Roczniki Chemii 30, 243 (1956). They are obtained, for example, by reaction of sulphinic acids or sulphinates with acrylonitrile in aqueous medium.

Preferred suitable 2,2-dihalogeno-3-sulphonyl-propionitriles for the process according to the invention are compounds of the formula $$R^2-SO_2-CH_2-CX_2^2-CN \qquad (III)$$

wherein $R^2$ denotes optionally substituted phenyl, naphthyl, benzyl, naphthylmethyl, straight-chain or branched lower alkyl such as methyl, ethyl, propyl, isopropyl, butyl, isobutyl, pentyl, isopentyl, hexyl and isohexyl, and cycloalkyl such as cyclopentyl and cyclohexyl, and $X^2$ denotes chlorine or bromine.

Particularly preferably suitable for the process according to the invention are 2,2-dihalogeno-3-sulphonyl-propionitriles of the formula $$R^3-SO_2-CH_2-CX_2^3-CN \qquad (IV)$$

wherein $R^3$ denotes phenyl, benzyl, methyl, ethyl and cyclohexyl, and $X^3$ denotes chlorine.

The following 2,2-dihalogeno-3-sulphonyl-propionitriles are mentioned as examples: 2,2-dichloro-3-phenyl-sulphonyl-propionitrile, 2,2-dichloro-3-benzyl-sulphonyl-propionitrile, 2,2-dichloro-3-methyl-sulphonyl-propionitrile, 2,2-dichloro-3-(3-chloro)-phenyl-sulphonyl-propionitrile, 2,2-dichloro-3-(3,4-dichloro)-phenyl-sulphonyl-propionitrile, 2,2-dichloro-3-(4-methyl)-phenyl-sulphonyl-propionitrile, 2,2-dibromo-3-phenyl-sulphonyl-propionitrile, 2,2-dibromo-3-benzyl-sulphonyl-propionitrile, 2,2-dibromo-3-methyl-sulphonyl-propionitrile, 2,2-dibromo-3-iso-propyl-sulphonyl-propionitrile and 2,2-dibromo-3-cyclopentyl-sulphonyl-propionitrile.

According to the process according to the invention, the treatment is always carried out with an excess of water. The molar ratio of 2,2-dihalogeno-3-sulphonyl-propionitriles to water varies in general in a range from 1:5 to 1:550.

In a preferred embodiment of the process according to the invention, the treatment with water is carried out without organic solvents. In general, in this case, 5 to 100 mols, preferably 10 to 50 mols, particularly preferably 15 to 30 mols, of water per mol of 2,2-dihalogeno-3-sulphonyl-propionitrile are employed. The process can be and is usually carried out without the co-presence of a base.

For example, in the case in which the treatment is carried out in the presence of an organic solvent, the quantity of water is 10 to 530 mols, preferably 15 to 160 mols, particularly preferably 25 to 100 mols, per mol of 2,2-dihalogeno-3-sulphonyl-propionitrile.

The following are mentioned as examples of organic solvents: aliphatic and aromatic hydrocarbons, such as paraffins, cyclohexane, benzene and toluene, alkylbenzenes, such as xylenes and cumene, halogeno hydrocarbons, such as dichloromethane, chloroform, dichloroethane, trichloroethylene and tetrachloroethylene, ethers, such as diethyl ether, methyl-tert.-butyl ether, tetrahydrofuran and dioxane, ketones, such as acetone, methyl ethyl ketone, methyl isobutyl ketone and cyclohexanone, esters, such as ethyl acetate and butyl acetate, alcohols, such as methanol, ethanol and isopropanol, glycols, such as ethylene glycol, glycol ethers and glycol esters, such as glycol monomethyl ether.

It is, of course, possible to use mixtures of the solvents. In this case, a homogeneous mixture or a mixture with several phases can result.

In general, 100 to 1,000 ml, preferably 250 to 600 ml, of organic solvent are optionally employed per mol of 2,2-dihalogeno-3-sulphonyl-propionitrile.

In general, the process according to the invention is carried out in the temperature range of from 20° to 130° C., preferably from 50° to 120° C. In carrying out the process according to the invention without organic solvent and with an excess of water, the reaction is preferably carried out in the boiling range of the water at normal pressure.

The process according to the invention can be carried out at reduced pressure, normal pressure or elevated pressure, for example, from 0.5 to 3 bars. Preferably, the process is carried out at normal pressure.

The reaction time of the process according to the invention is, in general, about 8 to 20 hours. The reaction time can be shortened to 5 to 12 hours if the reaction is carried out in the boiling range of water at normal pressure. The end of the reaction can be determined by analytical methods, for example, thin layer chromatography or high pressure liquid chromatography.

In a preferred embodiment of the process according to the invention, the 2,2-dihalogeno-3-sulphonyl-propionitriles are prepared by halogenation of 3-sulphonyl-propionitriles. The 3-sulphonyl-propionitriles are preferably obtained by reaction of sulphinates with acrylonitrile.

Within the scope of this preferred embodiment, the 2,2-dihalogeno-3-sulphonyl-propionitriles are obtained by reacting 3-sulphonyl-propionitriles of the formula

$$R^1-SO_2CH_2CH_2CN \qquad (V)$$

wherein $R^1$ has the meaning given above, with a halogenating agent, such as a sulphuryl halide, a phosphorus pentahalide or a halogen, optionally in a solvent, at a temperature of 30° to 130° C.

Sulphuryl chloride, phosphorus pentachloride, chlorine or bromine are preferably, chlorine very particularly preferably, used as the halogenating agent.

In general, 2 to 4 mols of halogenating agent are used per mol of 3-sulphonyl-propionitrile. 2 mols to 3 mols of halogenating agent are preferably used.

The halogenating agent is preferably added in such a quantity which reacts with the 3-sulphonyl-propionitrile and which does not lead to a concentration of halogenating agent in the reaction mixture.

In order to suppress the formation of by-products, it can be of advantage in carrying out the halogenation to discontinue the reaction when the 3-sulphonyl-propionitrile employed is not yet fully exhausted. Thus, for example, the reaction can advantageously be discontinued when a conversion of 30 to 95% is achieved.

The halogenation can be carried out without solvent or in a solvent which is customary for halogenation processes, for example a halogeno hydrocarbon such as dichloromethane, chloroform, dichloroethane, trichloroethylene or tetrachloroethylene.

The 2,2-dichloro-3-sulphonyl-propionitriles are particularly preferably prepared in the process according to the invention by carrying out the chlorination with chlorine in the temperature range from 80° to 120° C. without solvent.

In the preferred preparation of the 2,2-dihalogeno-3-sulphonyl-propionitriles, 2,3-dihalogeno-3-sulphonyl-acrylonitriles of the formula

$$R^1-SO_2CX^1=CX^1-CN \qquad (VI)$$

wherein $R^1$ and $X^1$ have the meaning given above, are obtained as by-product (up to about 10% by weight).

The 2,2-dihalogeno-3-sulphonyl-acrylnitriles and 2,3-dihalogeno-3-sulphonyl-propionitriles thus obtained can be employed in the process according to the reaction without further purification. Of course, it is also possible to follow up the halogenation with one of the customary working-up methods, for example crystallization or distillation. In this process, the 2,2-dihalogeno-3-sulphonyl-propionitriles and the 2,3-dihalogeno-3-sulphonyl-acrylonitriles can be purified and/or separated.

In general, it is expedient not to separate the reaction mixture, but to use it further as a mixture.

The 3-sulphonyl-propionitriles employed in the halogenation can be obtained by reaction of sulphinates of the formula

$$(R^1-SO_2)_nM \qquad (VII)$$

wherein $R^1$ has the meaning given above,

M represents hydrogen, ammonium or a metal and n gives the valency of M, in water, optionally in the presence of an organic solvent, with acrylonitrile, with simultaneous addition of acid.

Metals of the radical M are, for example, alkali metals, such as sodium or potassium, alkaline earth metals, such as magnesium or calcium, or divalent transition metals, such as zinc.

Solvents which are inert under the reaction conditions can be used as organic solvents. For example, the same solvents can be used as can be added as solent in the reaction according to the invention of the 2,2-dihalogeno-3-sulphonyl-propionitriles with water.

Of course, mixtures of these solvents with one another can also be used, and a homogeneous mixture or a mixture with several phases can result.

The reaction is preferably carried out in water without organic solvent.

The sulphinates can be present in fully dissolved or partially dissolved form. To achieve better space/time yields, the sulphinates are employed in partially dissolved form.

The reaction of the sulphinates with the acrylonitrile can be carried out in the temperature range of from 0° to 130° C. The reaction is preferably carried out at 50° to 120° C., particularly preferably at 90° to 110° C.

In the reaction of the sulphinates with acrylonitrile, an approximately constant pH value can be maintained by continuous addition of acids. A pH value preferably from 3 to 8, particularly preferably from 6 to 7, is maintained.

In general, organic and inorganic Brönstedt acids can be used as acids.

The following may be mentioned as organic Brönstedt acids: alkanoic acids, such as, for example, acetic acid, propionic acid and butyric acid, dicarboxylic acids, such as oxalic acid, malonic acid or succinic acid, aromatic carboxylic acids, such as benzoic acid and salicylic acid, sulphonic acids, such as methanesulphonic acid, ethanesulphonic acid, benzenesulphonic acid or toluenesulphonic acid The following may be mentioned as inorganic Brönstedt acids: aqueous solutions of sulphuric acid, hydrogen halide acids such as hydrochloric acid, phosphoric acid, sulphurous acid or carbon dioxide.

The Brönstedt acids are preferably employed in the concentration range of 20 to 70%. 40 to 60% strength sulphuric acid is particularly preferably employed.

In general, the sulphinates are initially taken and the acrylonitrile is added to the extent to which it reacts. The acid is added simultaneously with the acrylonitrile, in such a manner that a constant pH range according to the invention is maintained.

The working-up of the reaction mixture can, for example, be effected by phase separation, by extraction or by crystallization. The reaction mixture is preferably worked up with the aid of a phase separation. The phase separation can be effected with the product itself, liquefied by elevation of temperature, or with the aid of an organic solvent added before, during or after the reaction. For example, if water is used as the reaction medium, water-immiscible organic solvents or organic solvents which are only miscible with difficulty with water can be employed. Aromatic hydrocarbons, such as toluene or xylenes, can be preferably employed as organic solvents.

If the reaction is carried out in water as solvent, for example with very high concentration of sulphinates and acrylonitrile, in addition to the two liquid phases, as appropriate, a further solid phase can be obtained, by precipitated salts. In this case, these salts can be removed by rinsing, for example with water.

The reaction products are obtained with high purity, so that they can be used for the halogenation, without further purification steps. But it is, of course, possible to purify the reaction products more extensively, before further use, for example by distillation or crystallization.

In a very particularly preferred embodiment of the process according to the invention, the 2-halogeno-3-sulphonyl-acrylonitriles can be prepared, starting from the sulphinates and acrylonitrile, without isolation of intermediate products, in a one-pot reaction, which is characterized in that the sulphinates are reacted with acrylonitrile in a first reaction step, and in a second reaction step the 3-sulphonyl-propionitriles obtained are halogenated and the 2,2-dihalogeno-3-sulphonyl-propionitriles obtained are treated with water. The 2-halogeno-3-sulphonyl-acrylonitriles thus obtained can contain 2,3-dihalogeno-3-sulphonyl-acrylonitriles.

It is surprising that in the reaction of the 2,2-dihalogeno-3-sulphonyl-propionitriles with water, according to the invention, a cleavage of hydrogen halide occurs and the nitrile groups remain unchanged. It was to be expected that the nitrile groups would be hydrolyzed by the water in the presence of the hydrogen halide formed.

In the preferred preparation of the 2,2-dihalogeno-3-sulphonyl-propionitriles, it was surprising that they can be prepared with high selectivity by halogenation of the 3-sulphonyl-propionitriles.

In the preferred preparation of the 3-sulphonyl-propionitriles, it was surprising that they can be obtained in high yield in the reaction of the sulphinates with acrylonitriles at temperatures of from 80° to 120° C.

According to the process according to the invention, 2-halogeno-3-sulphonyl-acrylonitriles are obtained which, as is known from German Offenlegungsschrift No. 2,500,265, are microbicidally active compounds.

The mixtures of 2-halogeno-3-sulphonyl-acrylonitriles and the by-product 2,3-dihalogeno-3-sulphonyl-acrylonitriles can be preferably used in microbicidal agents for the protection of industrial materials. These mixtures contain, in general, up to 20% by weight of 2,3-dihalogeno-3-sulphonyl-acrylonitriles, preferably 1 to 10% by weight (relative to 2-halogeno-3-sulphonyl-acrylonitrile).

The microbicidal action of the two components in the mixture is greater than that of the individual compounds. Industrial materials, e.g. non-living materials, which it is intended to protect from a microbial transformation and destruction by means of the active compounds according to the invention are, for example, adhesives, glues, papers and cartons, textiles, leather, wood, painting agents, building materials, rubber and plastic articles, materials for decorating rooms, such as carpets and curtains, cooling lubricants and cutting oils, which can be decomposed by microorganisms. In the scope of the materials to be protected, parts of production plants, for example cooling water circulations, may be mentioned, which can be impaired by microorganisms.

Microorganisms which can cause a disintegration or a transformation of the industrial materials are, for example, bacteria, fungi, yeasts, algae, muci and viruses. The active compound mixture, according to the invention, of 2-halogeno-3-sulphonyl-acrylonitriles and 2,3-dihalogeno-3-sulphonyl-acrylonitrile is preferably active against fungi and bacteria.

Microorganisms of the following genera may be mentioned as examples: Escherichia, such as *Escherichia coli*, Pseudomonas, such as *Pseudomonas aeroginosa*, Staphylococcus, such as *Staphylococcus aureus*, Alternaria, such as Alternaria tenues, Aspergillus, such as *Aspergillus niger*, Chaetomium, such as *Chaetomium globosum*, Coniofora, such as *Coniofora cerebella*, Lentinus, such as *Lentinus tigrinus*, Penicillium, such as *Penicillium glaucum*, Polyporus, such as *Polyporus versicolor*, Pullularia, such as *Pullaria pullulans*, Solerofoma, such as *Solerofoma pytholofila* and Trichoderma, such as *Trichoderma viride*.

According to their area of application, the active compounds according to the invention can be converted into the customary formulations, such as solutions, emulsions, suspensions, powders, pastes and granules. These formulations can be prepared in a manner which is in itself known, for example, by mixing the active compounds with an extender of liquid solvent and/or solid carrier materials, if appropriate using surface-active agents, such as emulsifiers and/or dispersing agents, and, for example, in the case where water is used as extender, organic solvents can be used as auxiliaries, if appropriate. Examples of liquid solvents or active compounds can be water, alcohols, for example lower aliphatic alcohols, preferably ethanol and isopropanol, araliphatic alcohols, such as benzyl alcohol, liquid hydrocarbons, such as petroleum fractions, chlorinated hydrocarbons, such as 1,2-dichloroethane, glycols and polyglycols, esters such as ethyl acetate, amylacetate and butylacetate, glycol ethers, such as methyl glycol ether and phenyl glycol ether, ketones, such as cyclohexanone and methyl ethyl ketone, acid amides and acid amide derivatives, such as dimethylformamide, and nitriles, such as acetonitrile.

Examples of solid carrier materials, which are added in the preparation of the finished use forms of the active compound, can be talc, kieselguhr, bentonite, kaolin, diatomaceous earth and ground synthetic minerals.

Surface-active agents can be commercially customary emulsifiers, such as alkylsulphonates, alkylarylsulphonates, alkylsulphates, alkylamidesulphonates, alkylarylpolyether alcohols and polyoxyethylene fatty acid esters, or dispersing agents, such as lignin, methylcellulose; polyoxyethylene-polyoxypropylene and block polymers.

The use form of the microbicidal agent according to the invention contains, in general, 1 to 95% by weight, preferably 5 to 50% by weight, of the 2-halogeno-3-sulphonyl-acrylonitrile according to the invention, preferably with 1 to 10% by weight of 2,3-dihalogeno-3-sulphonyl-acrylonitrile (% by weight reltive to the 2-halogeno-3-sulphonyl-acrylonitrile employed) as the active compound.

The quantities of the use form of the active compound in the protection of industrial materials can be varied in relatively large ranges. In general, they are in the range from 0.0001 to 1% by weight, preferably in the range from 0.001 to 0.1% by weight, relative to the total amount of the material to be protected.

The active compounds according to the invention can be present in the formulations in mixtures with other known active compounds. The following active compounds are mentioned as examples: benzimidazolyl-methylcarbamate, tetramethyl-thiuramdisulphide, N-fluorodichloromethyl thiophthalimide and N,N'-dimethyl-N'-phenyl-(N-fluorodichloromethylthio)-sulphamide.

EXAMPLES

A 2 l four-necked flask is equipped with a stirrer, reflux condenser, thermometer, pH-electrodes and two 500 ml dropping funnels.

EXAMPLE 1

(a) Preparation of 3-sulphonyl-propionitrile 650 ml of water are introduced into the flask and are heated to 80° to 90° C., and 935 g (4 mols) of 70% strength sodium benzenesulphinate are added to the water. 215 g (4.04 mols) of acrylonitrile and 382 g (1.95 mols) of 50% strength sulphuric acid are then added simultaneously, in the course of about 1 hour at 100° C., at such a rate that the pH value remains at 6 to 7. The mixture is stirred for 30 minutes at 100° C. and the pH value is again readjusted. Excess acrylonitrile is distilled off over a Vigreux column in an azeotropic mixture with water at normal pressure, and 255 g of xylene are then added and the phases are separated at about 95° C. This is carried out by sucking off the lower aqueous phase with a suction tube. The salt precipitate remains for the most part in the flask. 800 ml of washing water is now stirred in at >95° C. and the phases are separated as described above. In this process most of the salt is dissolved, and the remainder does not interfere in the following reaction. A further 17 g of 3-phenylsulphonyl-propionitrile are isolated from the combined aqueous phases. 255 g (300 ml) of xylene are now added to the organic phase in the flask, at 95° to 100° C., and the remaining water is distilled off azeotropically with xylene (boiling point 92° C.) The remaining xylene is completely removed in vacuo at a trough temperature of 100° to 120° C. The trough now contains 730 g (94%) of 3-phenylsulphonyl-propionitrile in 97% purity, and 50 g of salt.

(b) Reaction of 3-phenyl-sulphonylpropionitrile with $Cl_2$

An inlet tube with a frit attachment is now introduced into the flask, without cooling, and 531 g (7.47 mols) of chlorine are introduced at 110° to 120° C. in the course of 6 to 10 hours, whilst stirring very vigorously. The conversion is monitored by means of analytical thin layer chromatography (mobile solvent toluene/ethyl acetate 9:1), and chlorine (approximately 50 g = 0.7 mol) is further introduced to replace portions of chlorine entrained by HCl. Excess chlorine and HCl are now removed in the course of 30 minutes by evacuation at 110° C. 958 g (97%) of 2,2-dichloro-3-phenylsulphonyl-propionitrile, which contains approximately 5% of 2,3-dichloro-3-phenyl-sulphonyl-acrylonitrile, remain in the flask.

(c) Reaction of a mixture of 2,2-dichloro-phenyl-sulphonyl-propionitrile and 2,3-dichloro-phenylsulfonyl-acrylonitrile with water 1,200 ml of water are added to the flask at approximately 100° C. The mixture is boiled under reflux for 12 hours (trough temperature approximately 120° C.), whilst stirring, the (top) aqueous phase is then separated off at 90° to 100° C. and the organic phase is freed from remnants of water at 90° to 100° C. in vacuo. 820 g (90%) of a pale brown melt are obtained, which solidifies on cooling into a wax-like substance. A content of 90 to 98% of 2-chloro-3-phenylsulphonyl-acrylonitrile (cis- and trans-form) and 2 to 10% of 2,3-dichloro-3-phenylsulphonyl-acrylonitrile is determined by HPLC.

EXAMPLES 2 TO 5

The following compounds are prepared in the same manner as in Example 1:

|    |                                                      | Melting point |
|----|------------------------------------------------------|---------------|
| 2. | 2-Chloro-3-(3-chloro-phenyl)-sulphonyl-acrylonitrile | 150° C.       |
| 3. | 2-Chloro-3-methyl-sulphonyl-acrylonitrile            | 53° C.        |
| 4. | 2-Chloro-3-(4-methyl-phenyl)-sulphonyl-acrylonitrile | 78° C.        |
| 5. | 2-Chloro-3-(3,4-dichloro-phenyl)-sulphonyl-acrylontrile | 107° C.    |

What is claimed is:

1. A process for the preparation of a 2-halogeno-3-sulphonyl-acrylonitrile of the formula

wherein $R^1$ denotes $C_6$ to $C_{18}$ aryl, aralkyl where the aromatic portion has up to 10 carbon atoms and the alkyl portion has up to 6 carbon atoms, $C_1$ to $C_{12}$ alkyl or $C_6$ to $C_{17}$ cycloalkyl, any of which radicals can optionally be substituted by a radical which does not change during the process and $X^1$ denotes halogen, which comprises contacting a 2,2-dihalogeno-3-sulphonyl propionitrile of the formula

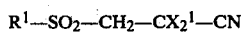

wherein R¹ and X¹ have the meaning given above with a composition consisting essentially of water in a stoichiometric excess at a temperature of 20°–130° C., employing a molar ratio of 2,2-dihalogeno-3-sulphonyl-propionitrile to water of 1:5–550 at pressure of at least 0.5 bar whereby a halogen halide is formed additionally.

2. A process according to claim 1, wherein the process is carried out in the presence of an inert organic solvent.

3. A process according to claim 1 wherein the reaction is carried out without organic solvent at a temperature in the range of the boiling point of water.

* * * * *